United States Patent [19]

Laanio et al.

[11] Patent Number: 4,490,372
[45] Date of Patent: Dec. 25, 1984

[54] SYNERGISTIC PESTICIDAL COMPOSITIONS COMPRISING FENVALERATE AND 2,4-DIAMINO-6-CYCLOPROPYLAMINO-S-TRIAZINE OR 2,4-DIAMINO-6-ISOPROPYLAMINO-S-TRIAZINE

[75] Inventors: Verena Laanio, Arisdorf; Marcus von Orelli, Münchenstein; Walter Häusermann, Monthey, all of Switzerland

[73] Assignee: Ciba-Geigy Corporation, Ardsley, N.Y.

[21] Appl. No.: 518,263

[22] Filed: Jul. 28, 1983

Related U.S. Application Data

[63] Continuation of Ser. No. 321,843, Nov. 16, 1981, abandoned.

[30] Foreign Application Priority Data

Nov. 25, 1980 [CH] Switzerland ............... 8704/80
Nov. 25, 1980 [CH] Switzerland ............... 8707/80

[51] Int. Cl.³ ............... A01N 43/64; A01N 37/34
[52] U.S. Cl. ............................. 424/249; 424/304
[58] Field of Search ............... 424/249, 304

[56] References Cited

U.S. PATENT DOCUMENTS

| 4,225,598 | 9/1980 | Brechbühler et al. | 424/249 |
| 4,308,262 | 12/1981 | Badmin et al. | 424/304 |
| 4,312,816 | 1/1982 | Aketa et al. | 424/304 |
| 4,321,212 | 3/1982 | Suzuki et al. | 424/304 |
| 4,346,092 | 8/1982 | Sanborn | 424/304 |

FOREIGN PATENT DOCUMENTS 0857896 2/1978 Belgium .
2805226 8/1978 Fed. Rep. of Germany .
1439615 6/1976 United Kingdom .

OTHER PUBLICATIONS

Borkovec et al., "Insect Chemosterilants v. Derivatives of Melamine", J. Med. Chem. 10, (1976), pp. 457-461.
Elliott et al., "A Photostable Pyrethroid", Nature, vol. 246, (1973), pp. 169-170.
Pesticide Manual, 6th Ed., (1979), pp. 143-144.
Abstract, Japanese Kokai 73-52937, Chem. Abstr. 79, 122576u, (1973).

Primary Examiner—Jerome D. Goldberg
Assistant Examiner—John M. Kilcoyne
Attorney, Agent, or Firm—Frederick H. Rabin

[57] ABSTRACT

The invention relates to an insecticidal and acaricidal composition which contains a combination of a compound of the formula I

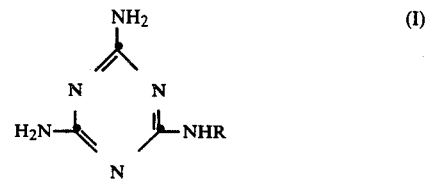

in which R is a cyclopropyl or an isopropyl group, and one of the following components: α-cyano-3-phenoxybenzyl 3-(1,2-dibromo-2,2-dichloroethyl) 2,2-dimethylcyclopropanecarboxylate, 3-phenoxybenzyl(1RS)-cis,-trans-3-(2,2-dichlorovinyl)-2,2-dimethylcyclopropanecarboxylate, 1H-indene-1-spiro-1'-[2,2-dimethyl-3-({α-cyano-3-phenoxybenzyl}-oxy)carbonyl cyclopropane], (RS)-α-cyano-3-phenoxybenzyl (RS)-2-(4-chlorophenyl)-3-methylbutyrate, and (RS)-α-cyano-3-phenoxybenzyl (1RS)-cis,trans-3-(2,2-dichlorovinyl)-2,2-dimethylcyclopropanecarboxylate.

6 Claims, No Drawings

SYNERGISTIC PESTICIDAL COMPOSITIONS COMPRISING FENVALERATE AND 2,4-DIAMINO-6-CYCLOPROPYLAMINO-S-TRIAZINE OR 2,4-DIAMINO-6-ISOPROPYLAMINO-S-TRIAZINE

This is a continuation of application Ser. No. 321,843 filed on Nov. 16, 1981, now abandoned.

The present invention relates to novel insecticidal and acaricidal compositions which contain an active ingredient combination, together with one or more inert adjuvants, and to the use of said combination, or of a composition containing it, for controlling insects and mites of the order Acarina.

The control of pests is increasingly giving rise to serious problems which involve environmental pollution on the one hand, and the development of resistance on the other. Although a wide range of pesticides is available, increasing environmental pollution puts a limit to the use of chemical substances. However, if there is no longer any guarantee of the total destruction of a pest population, including its various development stages, as a consequence of low rates of application, then the development of resistance to the chemicals employed is promoted. This resistance leads to the build-up of pest populations which are not adequately controlled, or which can no longer be controlled at all, by the compounds originally employed. Resistance can be built up not only to individual compounds, but also to classes of compounds. It is therefore desirable in pest control to use compositions which hinder the development of resistance when employed in environmentally tolerable rates of application.

Accordingly, it is an object of the present invention to provide compositions for controlling insects and mites of the order Acarina, in particular parasitic mites and, most particularly, mites which are parasites of animals, with which compositions pests are effectively controlled using environmentally tolerable rates of application, while substantially avoiding the development of resistance.

The compositions of the present invention contain an active ingredient combination which consists of a compound of the formula I

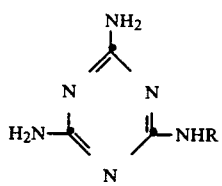

in which R is a cyclopropyl or an isopropyl group, and a compound selected from the group consisting of α-cyano-3-phenoxybenzyl 3-(1,2-dibromo-2,2-dichloroethyl) 2,2-dimethylcyclopropanecarboxylate of the formula IIa

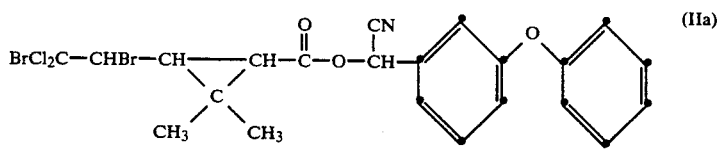

3-phenoxybenzyl (1RS)-cis,trans-3-(2,2-dichlorovinyl)-2,2-dimethylcyclopropanecarboxylate of the formula (IIb)

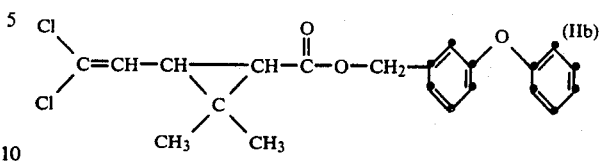

1H-indene-1-spiro-1'-[2,2-dimethyl-3-({α-cyano-3-phenoxybenzyl}-oxycarbonyl)-cyclopropane] of the formula IIc

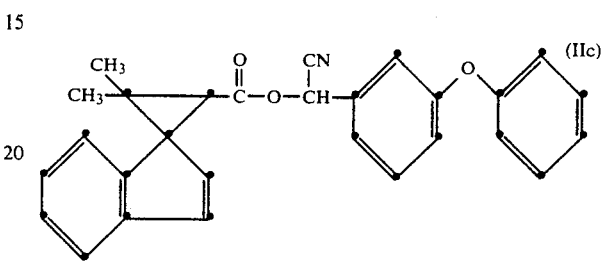

(RS)-α-cyano-3-phenoxybenzyl (RS)-2-(4-chlorophenyl)-3-methylbutyrate of the formula IId

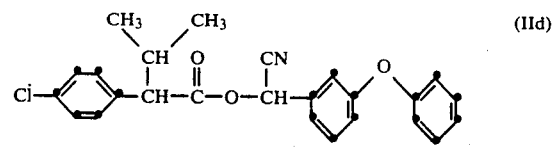

and (RS)-α-cyano-3-phenoxybenzyl (1RS)-cis,trans-3-(2,2-dichlorovinyl)-2,2-dimethylcyclopropanecarboxylate of the formula IIe

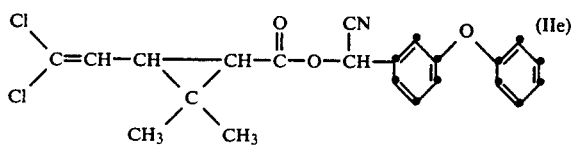

The individual compounds of which the active ingredient combination is composed are known pesticides and can be prepared by known methods.

The compound of the formula I, in which R is a cyclopropyl group, is described in Belgian patent specification 857 896; and the compound of the formula I, in which R is an isopropyl group, is known from J. Med. Chem. 10 (1967), 457. The compound of the formula (IIa) is disclosed in German Offenlegungsschrift No. 2 805 226. The compound of the formula IIb is disclosed in Nature (London), 1973, 246, 169, and is known as permethrin. The compound of the formula IIc is disclosed in U.S. patent specification 3 966 959 and is known as cypothrin. The compound of the formula IId is disclosed in British patent specification No. 1 439 615 and is known as fenvalerate. The formula IIe is disclosed in the Pesticide Manual, 6th Ed., 1979, and is known as cypermethrin.

Surprisingly, it has now been found that the active ingredient combination in the compositions of the invention has a synergistic effect, i.e. that it significantly exceeds the additive effect of the individual components.

The weight ratio of a compound of the formula I to a compound of the formula IIa, IIb, IIc, IId or IIe in the active ingredient combinations of the invention is in the range from 1:100 to 100:1. To bring about the synergistic effect, the preferred range is from 1:10 to 10:1.

The invention on which the compositions are based is illustrated by the following Example. The determination of the synergistic effect is carried out by the method of Y. P. Sun and E. R. Johnson for determining the biocidal activity of compound mixtures on specific species [J. Econ. Entomol. 53, 887 (1960)]. In this method, the synergistic effect of the combination of active ingredients is determined by comparing the dose-/action curves of the combinations and their individual components, using the co-toxicity indices, and is calculated as follows:

$$\text{co-toxicity index } CI = \frac{IR_{50} \text{ theory}}{IR_{50} \text{ test}}.$$

In this equation, $IR_{50}$ denotes the concentration of the active ingredients, or combinations thereof, in ug/ml at which no reproduction of 50% of the test organisms takes place.

The theoretical $IR_{50}$ value expected of an active ingredient combination is based on the assumption of an additive effect of both the individual components and is calculated by the formula for the harmonic mean:

$$IR_{50} \text{ theory} = \frac{1}{\frac{a}{IR_{50}A} + \frac{b}{IR_{50}B}},$$

wherein a is the proportion of compound A and b the proportion of compound B, relative to the total weight of the combination $A + B$.

Active ingredient combinations with a synergistic, i.e. more than additive, action of the two individual components give co-toxicity indices with values of $>1$.

EXAMPLE 1

Fully replete ticks (Boophilus microplus ♀♀) of the organophosphorus-resistant strain Biarra, in groups of 40, are fixed in the dorsal position in Petri dishes of 9 cm diameter and treated with freshly prepared solutions or suspensions of the active ingredients and of active ingredient combinations in standard WHO water. Sufficient liquid is poured into each dish that the ticks are completely immersed. After 1 hour the liquid is poured off and any drops still remaining are shaken off. The Petri dishes with the ticks are then dried overnight at room temperature and subsequently incubated for 4 weeks at 28° C. and 80% relative humidity until oviposition has taken place and the larvae have hatched out.

The criteria used for evaluating the activity of the tested compounds and compound mixtures are: the mortality and sterility of the treated female ticks as well as the inability of the eggs to hatch. These effects are used to evaluate the inhibition of reproduction (IR).

A dilution series at different concentrations is used for each active ingredient or combination of active ingredients, and the corresponding dose/action curves and the $IR_{50}$ are determined by the method of Berkson (J. Am. Stat. Assoc. 48, 565, 1953).

The co-toxicity values are then determined from the values obtained for $IR_{50}$ test and $IR_{50}$ theory (Table 1). Combinations of compounds of the formulae I, IIa and IId are tested.

Combination components:

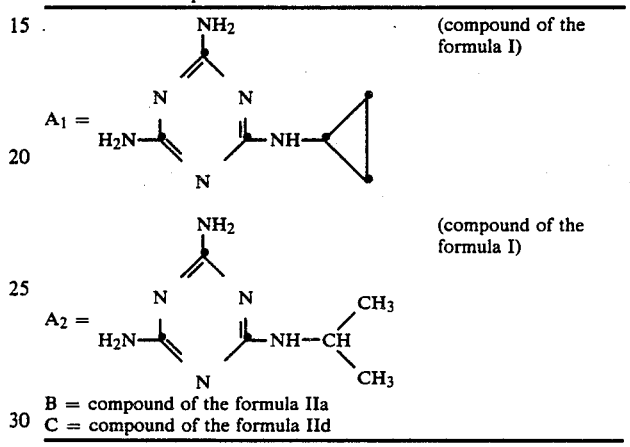

B = compound of the formula IIa
C = compound of the formula IId

TABLE 1

| Compound compound mixture | Weight ratio of the mixture | $IR_{50}$ test μg/ml | $IR_{50}$ theory μg/ml | Cotox. index |
|---|---|---|---|---|
| $A_1$ | — | >>15000 | — | — |
| B | — | 7.7 | — | — |
| $A_1$:B | 9:1 | 11.4 | 76.6 | 6.72 |
| $A_1$:B | 1:9 | 4.1 | 8.6 | 2.08 |
| C | — | 10.1 | — | — |
| $A_1$:C | 1:1 | 8.8 | 20.2 | 2.29 |
| $A_2$ | — | >>15000 | — | — |
| B | — | 7.7 | — | — |
| $A_2$:B | 9:1 | 10.6 | 76.6 | 7.23 |
| $A_2$:B | 1:1 | 5.2 | 15.4 | 2.96 |
| $A_2$:B | 1:9 | 4.0 | 8.6 | 2.15 |
| C | — | 10.1 | — | — |
| $A_2$:C | 1:1 | 9.9 | 20.2 | 2.03 |

For controlling insects and mites of the order Acarina, the active ingredient combinations can be used by themselves or in the form of compositions which contain an active ingredient combination together with one or more inert adjuvants. Suitable inert adjuvants are solid and liquid, natural or regenerated substances conventionally employed in the art of formulation, e.g. solvents, dispersants, wetting agents, tackifiers, thickeners or binders.

The active ingredient combinations can be processed to formulations such as dusts, emulsifiable concentrates, granulates, dispersions, sprays, solutions or suspensions. It is also possible to use liquid, in particular, aqueous preparations or concentrates of active ingredient combinations for plunge dips, spray races, pour on solutions and manual methods of application (handspray and hand-dressing).

The compositions of the present invention are conveniently prepared by intimately mixing and/or grinding the active ingredient combinations with suitable adjuvants, with or without the addition of dispersants or solvents which are inert to the active ingredients. The active ingredient combinations can be processed e.g. to the following formulations:

solid formulations: dusts, tracking powders, granulates:

liquid formulations:
(a) solutions
(b) water-dispersible concentrates of the active ingredient combinations: wettable powders, pastes, emulsions.

The compositions of the invention advantageously contain 2 to 80% by weight, preferably 5 to 50% by weight, of active ingredient combination.

EXAMPLE 2

Wettable powder

The following ingredients are intensively mixed in a mixing apparatus: 5 to 50 parts of an active ingredient combination, 5 parts of an absorbent carrier (silica gel K 320 or Wessalon S), 35 to 80 parts by weight of a carrier (Bolus alba or kaolin B 24) and a dispersing agent mixture consisting of 5 parts of a sodium laurylsulfonate and 5 parts of an alkylaryl polyglycol ether. This mixture is ground to a granular size of 5–15 μm in a disc attrition mill or air jet mill. The resultant wettable powder gives a good suspension in water.

EXAMPLE 3

Dust

The following ingredients are intensively mixed: 5 parts by weight of a finely ground active ingredient combination, 3 parts by weight of precipitated silicic acid, and 92 parts by weight of talc.

The active ingredient combinations and the compositions containing them have a pronounced activity against insects and against mites of the order Acarina, especially those forms which are parasites of animals. They are particularly effective against ticks and against insects of the order Diptera, in which connection their excellent action against Diptera belonging to the family Calliphoridae merits special mention. It is especially the larvae of these insects which can cause severe damage in animal husbandry and their control is consequently of the first importance. Most particularly, attention is drawn to the very good efficiency of the active ingredient combinations and of the compositions containing them in controlling representatives of the Lucilia belonging to the family Calliphoridae, especially of the species Lucilia sericata (blowfly).

What is claimed is:

1. A synergistic composition for controlling insects of the order Diptera and mites of the order Acarina, which compositions comprises a compound of formula I

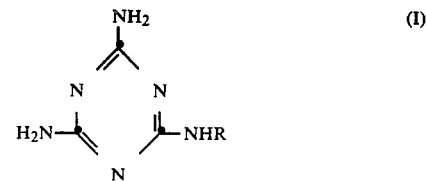

in which R is cyclopropyl or isopropyl, and the compound (RS-α-cyano-3-phenoxybenzyl (RS)-2-(4-chlorophenyl)-3-methylbutyrate of the formula IId

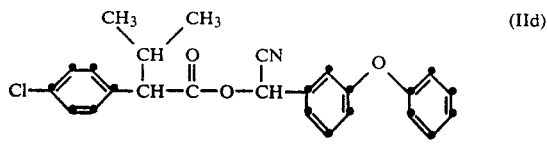

in which the ratio by weight of a compound of formula I to the compound of formula IId in the active ingredient combination is from 9:1 to 1:4.

2. A method for controlling insects of the order Diptera and parasitic mites belonging to the order Acarina, which comprises contacting said insects or mites or their habitats with an effective amount of a composition according to claim 1.

3. A method according to claim 2 for combatting ticks.

4. A method according to claim 2 for combatting insects of the order Diptera.

5. A method according to claim 4 for combatting insects of the order Diptera which belong to the family Calliphoridae.

6. A method according to claim 5 for combatting insects of the genus Lucilia belonging to the family Calliphoridae.

* * * * *